(12) United States Patent
Pearlman

(10) Patent No.: US 6,350,734 B1
(45) Date of Patent: *Feb. 26, 2002

(54) METHODS AND KITS FOR REMOVING, TREATING, OR PREVENTING LICE WITH DRIABLE PEDICULOSTATIC AGENTS

(76) Inventor: Dale L. Pearlman, 21063 Christensen Dr., Cupertino, CA (US) 95014

( * ) Notice: Subject to any disclaimer, the term of this patent is extended or adjusted under 35 U.S.C. 154(b) by 0 days.

This patent is subject to a terminal disclaimer.

(21) Appl. No.: 09/941,412

(22) Filed: Aug. 28, 2001

Related U.S. Application Data

(63) Continuation of application No. 09/842,762, filed on Apr. 25, 2001, which is a continuation of application No. 09/491,114, filed on Jan. 25, 2000, now Pat. No. 6,265,384
(60) Provisional application No. 60/117,318, filed on Jan. 26, 1999.

(51) Int. Cl.⁷ .......................... A61K 31/70; A61K 49/00
(52) U.S. Cl. ............................... 514/31; 424/9.6
(58) Field of Search ............................... 514/31; 424/9.6

(56) References Cited

U.S. PATENT DOCUMENTS

| | | |
|---|---|---|
| 3,341,465 A | 9/1967 | Kaufman et al. |
| 3,929,678 A | 12/1975 | Laughlin et al. |
| 3,959,461 A | 5/1976 | Bailey et al. |
| 4,165,369 A | 8/1979 | Watanabe et al. |
| 4,387,090 A | 6/1983 | Bolich, Jr. |
| 4,495,079 A | 1/1985 | Good |
| 4,610,806 A | 9/1986 | Rosen |
| 4,612,944 A | 9/1986 | Bachrach et al. |
| 4,913,893 A | 4/1990 | Varco et al. |
| 4,927,813 A | 5/1990 | Bernstein |
| 5,034,218 A | 7/1991 | Duvel |
| 5,066,481 A | 11/1991 | Helioff et al. |
| 5,284,833 A | 2/1994 | McAnalley et al. |
| 5,288,483 A | 2/1994 | Cardin et al. |
| 5,292,504 A | 3/1994 | Cardin et al. |
| 5,302,371 A | 4/1994 | Lamb et al. |
| 5,480,633 A | 1/1996 | Simion et al. |
| 5,562,912 A | 10/1996 | Burke et al. |
| 5,636,646 A | 6/1997 | Zito |
| 5,656,280 A | 8/1997 | Herb et al. |
| 5,681,546 A | 10/1997 | Lee et al. |
| 5,783,202 A | 7/1998 | Tomlinson et al. |
| 5,853,706 A | 12/1998 | Klar |
| 5,858,383 A | 1/1999 | Precopio |
| 5,972,987 A | * 10/1999 | Reid et al. .................. 514/407 |
| 5,997,846 A | * 12/1999 | Burns et al. ................. 424/9.6 |
| 5,997,847 A | * 12/1999 | Spiesel ....................... 424/9.6 |
| 6,001,339 A | 12/1999 | Finel et al. |
| 6,063,771 A | 5/2000 | Snyder |
| 6,139,859 A | 10/2000 | Precopio |
| 6,265,384 B1 | 7/2001 | Pearlman |
| 6,303,581 B2 | 10/2001 | Pearlman |

FOREIGN PATENT DOCUMENTS

| | | |
|---|---|---|
| BE | 868239 | 10/1978 |
| CA | 1 099 637 | 4/1981 |
| EP | 0 191 236 A1 | 8/1986 |
| EP | 0 803 192 A1 | 10/1997 |
| GB | 1532585 | 11/1978 |
| WO | WO 91/05561 | 5/1991 |
| WO | WO 99/18800 | 4/1999 |
| WO | WO 01/13954 | 3/2001 |

OTHER PUBLICATIONS

Clore et al., "A Comparative Study of Seven Pediculicides and Their Packaged Nit Removal Combs," *Journal of Pediatric Health Care*, 7(2): 55–60 (1993).

Fukushima et al., "The Effect of Cetostearyl Alcohol in Cosmetic Emulsions," *Cosmetics & Toiletries*, 98: 89–102 (1983).

Hunting, *Encyclopedia of Conditioning Rinse Ingredients*, p204 (1987).

Iannantuono et al., "Pediculicidal Activity of an Antidandruff Shampoo in a 1% Copper–Oleate Formulation," Advances in Therapy, 14(3): 134–139 (1997).

\* cited by examiner

*Primary Examiner*—Zohreh Fay
*Assistant Examiner*—Brian-Yong Kwon
(74) *Attorney, Agent, or Firm*—Daniel M. Becker; Fish & Neave

(57) ABSTRACT

Methods and kits for removing, treating or preventing head lice infestations in patients in need of such treatment are disclosed and include topically applying to the lice-infested area an effective amount of a driable pediculostatic agent for a time sufficient to immobilize the lice, drying the agent onto the application site and removing the dried agent, thereby removing the lice and nits.

39 Claims, No Drawings

METHODS AND KITS FOR REMOVING, TREATING, OR PREVENTING LICE WITH DRIABLE PEDICULOSTATIC AGENTS

CROSS-REFERENCE TO RELATED APPLICATIONS

The present application is a continuation of U.S. patent application Ser. No. 09/842,762, filed Apr. 25, 2001, now allowed, which is a continuation of U.S. patent application Ser. No. 09/491,114, filed Jan. 25, 2000, now U.S. Pat. No. 6,265,384 B1, which claims priority to U.S. provisional patent application No. 60/117,318, filed Jan. 26, 1999, the disclosures of which are incorporated herein by reference in their entireties.

FIELD OF THE INVENTION

The present invention relates to methods and kits for the diagnosis, treatment, removal or prevention of pedicular parasite infestations. More particularly, the methods and kits relate to the use of nontoxic driable agents that rapidly immobilize head lice and keep them immobilized when dried, in order to facilitate their removal from the hair and scalp. The methods and kits further relate to the use of driable agents that inhibit hatching of nits, obviating nit-picking and combing in the treatment of lice infestation.

BACKGROUND OF THE INVENTION

Pediculosis is a scalp infestation produced by *Pediculus humanus capitis*. Cases of pediculosis are quite frequent, both in their endemic and epidemic forms. As the lice feed on human skin and blood, they inject their digestive juices and fecal material into the skin. These materials, as well as the puncture wound itself, cause skin irritation and lesions from the resulting scratching, and can cause a serious infection with ganglionic inflammation. Lice are also vectors of certain diseases, such as exanthematic or epidemic typhus and recurrent fever.

The adult female louse has a life span of about one month and lays up to ten nits a day which are firmly attached to hair through an excreted cement. The nits hatch to release instars in about seven to nine days, and the instars become mature adults in another week. To cure someone of head lice requires an approach that eliminates all 3 stages of the louse life cycle.

Many currently utilized treatment methods are based on the application of pediculicides, which are toxic pharmaceutical agents that, when internalized, poison and kill lice. Typically, such pediculicidal agents enter via the respiratory spiracles, and once inside the louse, interfere with the function of a critical metabolic or physiological pathway, leading to death. Malathion, for example, inhibits acetylcholinesterase, disrupting signaling in the nervous system.

Examples of insecticidal agents used to treat lice are described in EP 0191236 and U.S. Pat. No. 5,288,483. A significant disadvantage of using these agents is that lice can become resistant. The need for further treatment increases the exposure to these harsh agents and increases the cost. Additionally, clinicians and parents are reluctant to treat children with agents that can also prove toxic to human beings. There are reports in the medical literature, for example, that children treated with lindane have developed seizures.

Moreover, many of these compounds have unpleasant odors or other undesirable properties, causing noncompliance by the patient, leading to re-infestation of the individual, and spreading of the infestation to others. In addition, the harshness of these agents make them unsuitable for use as prophylactics.

Home remedies such as application of corn oil, olive oil, eucalyptus oil, neem oil, coconut oil, mayonnaise, or petroleum jelly for a period of time sufficient to kill the lice (e.g. overnight) are not practical or completely effective.

A further disadvantage of prior methods is the requirement of removing the nits from the hair in a separate treatment step. The removal of nits has typically been done by hand using special fine-tooth combs. U.S. Pat. No. 4,927,813 teaches compositions containing formic acid that facilitate removal of nits from the hair; however, formic acid is a known caustic agent.

Use of combing alone to treat head lice has the disadvantage that the lice can hold onto the hair shafts using their claws or escape by crawling away from the area being combed. This labor intensive method requires daily combing, is painful, and is unpleasant since the lice are active, visible and crawling.

Heat has also been suggested as a means of killing head lice. However, its use has not been effective, due in part to the fact that crawling lice will rapidly move away from the heat source. Moreover, the temperatures needed to kill the lice, typically 140° F. or higher, can burn or scald the scalp.

The use of heat in conjunction with pediculicidal compositions is discouraged. Not only are some of the solvents used in the pediculicidal compositions inflammable at the temperatures necessary to kill the lice, but the heat may additionally degrade the active pediculicidal agents as well.

Thus, there remains a need in the art for methods and kits useful for treating and removing lice infestations that are easy to use, inexpensive, cosmetically attractive and effective against lice resistant to other treatments. Moreover, there remains a need for methods and kits that eradicate nits as well as adults and instars, and that can be used prophylactically to prevent initial infection or re-infestation. Accordingly, these are some of the objects of the present invention.

SUMMARY OF THE INVENTION

These and other objects are furnished by the present invention, which in one aspect provides a method for the treatment or removal of lice and/or nits, particularly head lice and/or nits, in animal subjects, including humans. According to the method, an effective amount of a driable pediculostatic agent is applied to a lice-infested area of an animal subject, preferably a human subject, for a time sufficient to trigger an immersion reflex in the lice. The driable pediculostatic agent is then dried, and the lice and/or nits removed prior to or concomitantly with removal of the dried agent.

In one embodiment, the dried agent is removed, along with lice and nits, by combing the hair with a fine-toothed delousing comb, preferably prior to shampooing or wetting the hair. In another embodiment, the dried agent is removed, along with lice, by washing the hair with water, optionally with the aid of soaps, shampoos, conditioners, etc. If the dried agent is removed by washing, nits are optionally removed by combing the washed hair with a fine-toothed delousing comb.

The driable pediculostatic agent can be dried with the application of heat or air-dried, depending upon the formulation. To avoid dilution of the pediculostatic agent, the agent is preferably applied to the dry hair of the lice-infested area, typically in an amount sufficient to completely soak or saturate the hair and skin.

Regardless of the method of removing the dried agent, the efficiency of nit and/or lice removal can be optionally increased by adding a combing step between applying and drying the driable pediculostatic agent. In this optional embodiment, the agent applied to the hair is allowed to remain on the hair for a period of time sufficient to trigger the immersion reflex in lice. While the wet agent is still in the hair, the hair can be combed with a fine-toothed delousing comb. The wet agent removed by combing can be conveniently collected on paper towels, which can be sealed in a plastic bag, conveniently a zipper-loc plastic bag. The agent remaining on the hair can then be dried onto the hair and scalp and removed as previously described. In this alternative embodiment, the wet agent collected on the paper towels can be inspected for the presence of lice and/or nits, thereby providing a convenient diagnostic means for monitoring the course of the treatment and/or the severity of the infestation.

A pediculostatic agent is one that elicits the "immersion reflex" in lice, whereby the lice become immobilized as a consequence of reflexes that have evolved to avoid suffocation. The lice remain immobilized while in contact with the driable pediculostatic agent in its wet form, and do not recover from the immersion reflex once the agent has been dried onto the lice. In a preferred embodiment of the method of the present invention, the driable pediculostatic agent induces the immersion reflex within about 2 hours, preferably within about 5 minutes and most preferably within about 6 seconds, and can be readily dried by air evaporation or by application of heat from, for example, a hair-drier or hair curlers.

In a preferred method, the dried agent is permitted to remain on the hair for a period of time sufficient to induce the immersion reflex in the substantial majority of lice, and thus is preferably at least as long, in minutes, as the Immersion Reflex Index of the pediculostatic agent being applied. Typically, the dried pediculostatic agent is permitted to remain on the hair for a time sufficient to kill at least some of the lice, prior to removal of the lice and/or dried agent by washing and/or combing, usually at least about 2 to about 8 hours, typically overnight.

The pediculostatic agents of the present invention also serve to prevent nit hatching during the period of contact with the nits.

In another aspect, therefore, the methods of the present invention are designed to obviate nit removal as an obligate component of treating lice infestation. In this aspect, driable pediculostatic agent is applied to a lice-infested area of the body, and after triggering the immersion reflex, is dried thereon. The dried pediculostatic agent is left in contact with the body for a prolonged period, at least about 8 hours, preferably at least about 24 hours, more preferably at least two days, most preferably a week, before removal of the agent and/or reapplication of the driable agent. Nit hatching is prevented for the duration of contact, and the embryos therein thus progressively killed, thus obviating nit removal as a requirement of cure.

Optionally, a conventional pediculicidal active ingredient can be incorporated into the pediculostatic formulations described herein. The pediculicidal active ingredients can be used at levels effective to achieve their intended result, typically from about 0.25 wt % to about 2.5 wt %. Non-limiting examples of suitable pediculicidal agents include natural or other pyrethrins, pyrethroids, permethrin, lindane, malathion, carbaryl, ivermectin and combinations thereof. Piperonyl butoxide can additionally be added at levels from about 1 wt % to 5 wt % to hinder the development of resistance of the lice to the pediculicidal additives.

In an alternative embodiment, a driable pediculostatic agent can be applied to the infested area first, followed by application of a pediculicidal composition according to the methods of the invention, or vice versa. If the pediculicidal agent is applied first, the hair of the infested area is preferably dried prior to application of the driable pediculostatic agent.

The driable pediculostatic agent is optionally combined with a dye or other visible marker for temporarily marking the treated area in order to verify that the agent has been applied. The dye is preferably a fluorescent dye or other agent which is detectable when dried onto the body, chitinous nits or hair.

In another aspect, the invention provides a kit for the treatment, removal or prevention of lice and/or nits. In one embodiment, the kit comprises an amount of a driable pediculostatic agent sufficient for at least one application packaged in association with instructions for use in methods for removing, treating or preventing lice as described herein. In another embodiment, the kit comprises an amount of a driable pediculostatic agent sufficient for at least one application and a comb, optionally a fine-toothed delousing comb for removing lice and nits. Alternatively, the above-described kits can contain individual components that when mixed together, with or without the addition of water or other solvents, provide an amount of a driable pediculostatic agent sufficient for at least one application. The kits can optionally contain additional components, such as shower caps or other non-absorbent coverings, pediculicidal agents, dyes that can be mixed with the pediculostatic agents, etc.

DETAILED DESCRIPTION OF THE INVENTION

The prior art teaches that topical agents to treat and cure head lice are pediculicidal: if lice are temporarily inactivated and later recover from exposure, the agent is considered ineffective by those skilled in the art.

Typically, such topical agents have included toxic agents that are well known to kill lice, such as natural pyrethrins, pyrethroids, permethrin, lindane, malathion, carbaryl, ivermectin and combinations thereof. These agents, once internalized, typically target and interfere with specific components of metabolic or other physiologic pathways, leading to death of the organism. Given the physiologic similarities among eukaryotes, many of these agents disrupt metabolic or physiologic pathways, and thus prove toxic, in human beings as well.

More recently, nontoxic agents not previously considered lousicidal have also been identified as having pediculicidal activity. U.S. Pat. No. 5,783,202 discloses nonresidual pediculicidal mousse compositions in which the mousse foaming agent alone is said to be pediculicidal, and further is said to act synergistically with known pediculicides such as pyrethrins to kill head lice and nits. U.S. Pat. No. 5,858,383 discloses compositions and methods in which a substantially air-impermeable liquid composition, left sufficiently long in contact with lice, is said to be effective as a lousicide.

None of the art teaches that compositions that stun or immobilize the lice can be used as effective treatments; in fact, the prior art teaches away from using such agents.

It has now been surprisingly discovered that driable pediculostatic agents can be used in novel methods for the treatment, removal and/or prevention of lice and/or nit infestations, overcoming the disadvantages of the prior art methods.

A pediculostatic agent is one that elicits the "immersion reflex" in lice. The immersion reflex is a self-preservation behavior that lice have evolved to protect themselves against drowning when, through actions of the host, they are immersed in water. Lice are obligate air breathers and cannot derive oxygen when underwater; the immersion reflex allows them greatly to increase the amount of time that they can survive without access to air. During submersion, the spiracles and tracheoles, through which lice breathe, become blocked by water. As the lice become anoxic, they rapidly switch into a state of profound suspended animation, decreasing their need for oxygen, thus prolonging their survival. They become completely immobile, unresponsive to stimuli, and even cease gut motility. If the reflex continues too long, however, the lice eventually run completely out of oxygen and die from anoxia.

A pediculostatic agent is one that elicits the "immersion reflex" in lice. A driable pediculostatic agent is one that triggers the immersion reflex when wet, and that maintains the lice in the immersion reflex when thereafter dried in situ.

In contrast to classic pediculicidal agents, which act biochemically to disrupt a vital physiologic function, pediculostatic agents (including driable pediculostatic agents) function mechanically to trigger a normal endogenous behavioral reflex.

The methods and kits of the invention take advantage of driable pediculostatic agents to induce and maintain the immersion reflex to provide regimens for lice and nit removal and treatment that are safe, effective, and non-toxic. Since the methods and kits do not require application of a toxic pediculicidal agent for success, they are highly unlikely to engender resistance in the lice. Moreover, since the methods and kits are non-toxic, they provide safe prophylactic treatment for the entire at-risk group, thereby providing effective means of eradicating lice outbreaks and re-infestations.

In general, the method of treating or removing lice and/or nits according to the present invention comprises applying a driable pediculostatic agent to a lice-infested area of the body, typically the scalp, and allowing the agent to remain in contact with the lice for a period of time sufficient to trigger the immersion reflex in the lice by oxygen deprivation. Depending on the composition of the driable pediculostatic agent, the agent is then dried by air evaporation or application of heat, typically by blow-drying the hair. The dried pediculostatic agent is then removed, along with the lice and/or nits, typically by rinsing, shampooing or combing with a fine-toothed delousing comb, or by a combination of the three.

The frequency of treatment or application ranges from once per day to once every 30 days, with a preferred schedule being 1 time per week, as further discussed below. However, the treatment can be repeated at intervals as necessary, and as desired to accommodate bathing, completely to remove the lice and/or nits, as further described below.

The treatment can also be used as needed as a prophylactic measure to prevent initial infestation or repeated as needed for persons at risk of re-infection. Because the driable pediculostatic agents of the invention are non-toxic and do not engender resistance, the treatment methods described herein can be repeated indefinitely, if necessary.

The ability of a pediculostatic agent to induce the immersion reflex will depend upon its composition, which is further discussed infra, and upon its concentration after contact with hair. As to the latter, those of skill will appreciate that hair can experience varying degrees of wetness—from complete dryness, to damp, to towel-dry, to wet, to dripping—and that the varying degrees of hair wetness will effect varying degrees of dilution of an agent applied thereto.

The degree to which the hair must be dry upon application of the driable pediculostatic agent can readily be determined for any such driable pediculostatic liquid composition by its ability, when applied to the hair at a given degree of wetness, to induce the immersion reflex in the lice present therein, which is a critical determinant of its efficacy. The immersion reflex can readily be ascertained by visual inspection of the lice in the hair using slight magnification: if the lice are immobile and do not avoid a comb, the agent is effective at the concentration achieved in situ; if the lice are motile and avoid combing, the agent is ineffective. Thus, as defined herein, "dry hair" refers to a degree of hair dryness that does not effect dilution of a desired pediculostatic agent applied thereto beyond the point at which the agent timely triggers the immersion reflex in lice.

Preferably, the driable pediculostatic agent is applied full strength, i.e., in substantially undiluted form. This can be accomplished by applying the agent to the dry hair of the infested area, preferably in an amount sufficient completely to soak or saturate the area and/or hair, and massaging the agent in. For full-strength application, the agent can be applied not only to hair that is completely dry, but also to hair that is moist or damp, and to hair that is substantially dry, such as is obtained by towel-drying the hair following shampooing. The preferred aspect of the invention is that the hair be sufficiently dry that the driable pediculostatic agent is not substantially diluted when applied to the hair. Hair of the appropriate level of dryness can be obtained by squeezing, toweling or otherwise drying wet hair until water ceases dripping from the hair. In particularly preferred embodiments of the invention, the driable pediculostatic agent is applied to towel dry hair, more preferably to completely dry hair. Thus, if the driable pediculostatic agent is applied following shampooing, the hair should be wrung out or towel dried, preferably completely dried, prior to application.

Following application, the agent is dried. Depending upon its composition, the driable pediculostatic agent is dried either by air-drying or with the aid of heat from, for example, a blow- or other hair-dryer, heat-based curlers, a curling iron, etc. Since lice will typically crawl away from heat applied by a blow-dryer or other hair implement, in embodiments utilizing heat drying it is important that the driable pediculostatic agent be permitted to remain on the hair in its wet form for a time period sufficient to trigger the immersion reflex before it is dried. Since the immersion reflex immobilizes the lice, they are unable to crawl away from the heat source. Moreover, it is important that the driable pediculostatic agent be composed of solvents and other ingredients that are not inflammable at the temperatures applied by the dryer. Thus, when heat-drying is used, the agent is preferably an aqueous-based or aqueous composition, although nonaqueous formulations that will not ignite at the drying temperature can also be used.

The time interval between applying the driable pediculostatic agent and then drying the agent depends upon the "Immersion Reflex Index" of the particular driable pediculostatic agent, which is defined as the time, in minutes, within which the immersion reflex is triggered in a louse upon being contacted with the agent. Typically, drying can be commenced after a period of time equal to the Immersion Reflex Index of the particular pediculostatic agent used. However, longer intervals between application and drying can be used, and in some cases are even preferred. Most preferably, the pediculostatic agent remains in the hair prior to drying for a period of time equal to about 1 to 100 times, even more preferably about 1 to 50 times, more preferably about 5 to 30 times the Immersion Reflex Index of the particular driable pediculostatic agent being used.

Whether air-drying or heat-drying the driable pediculostatic agent, excess agent can be removed from the hair prior to drying to reduce the amount of time necessary for the agent to dry. The agent should be permitted to remain on the hair for a time period sufficient to trigger the immersion reflex as described above prior to removal of excess agent.

Excess agent can be removed by a variety of means, including but not limited to, squeezing off the hair with hands and combing with a regular hair comb or delousing comb. Preferably, excess agent is removed by combing. Removing excess agent by toweling the hair is not recommended, as it has been discovered that toweling removes the agent from the lice and permits them to recover from the immersion reflex, thereby undermining the treatment regimen. If desired, the removed agent can be placed on a towel or other material or surface and inspected for lice and/or nits as a means of monitoring the progression of treatment regimen. When monitoring is desired, at least some of the excess agent should be removed with a fine-toothed delousing comb.

It should be noted that in order to remove nits, the hair must be combed at some point with a fine-toothed delousing comb. This combing can be done in conjunction with removal of excess agent in its wet form (described supra), after the agent has been dried onto the hair (described supra and further described infra), or even after the dried treatment agent has been completely removed. As it has been found that certain driable pediculostatic agents aid the removal of nits when in their wet form—that is, prior to drying—particularly the preferred CETAPHIL® Cleanser driable pediculostatic agents, in a preferred embodiment of the invention nits are removed by combing the hair with a delousing comb between application of the pediculostatic agent and its drying. Removing nits at this stage provides the added benefit that the removed agent can be inspected for lice and nits, permitting the infestation and effectiveness of the treatment to be monitored.

As further discussed infra, the time-consuming and unpleasant task of nit-removal, which is obligatory in prior art methods to prevent reinfestation of the treated patient, and which is desirable in certain of the embodiments of the present invention, as just described, is obviated in those embodiments of the present invention that prevent hatching of the nits for a period of time sufficient to kill the embryos therein.

Once the agent has been dried onto the lice, hair and scalp, the lice do not recover from the immersion reflex and remain immobilized. While not intending to be bound by any theory of operation, it is believed that when the driable pediculostatic agent is dried, non-volatile compounds in the agent deposit onto the lice, thereby encasing, encapsulating, enveloping, enwrapping or otherwise covering the lice in a film or coating that prevents them from recovering from the immersion reflex even though they are dry.

If lice are encased in a film of dried pediculostatic agent for a sufficiently long duration, they suffocate and die. Because the mechanism of death so differs from that wrought by conventional pediculicides, however—through the mechanical, surface-occlusive induction of a normal endogenous reflex, rather than the biochemical disruption of a physiologic pathway—the term "pediculicide" is reserved herein for agents that act biochemically within the louse to disrupt metabolic or physiological pathways, leading to death.

While killing the lice is not necessary for success of the methods described herein, in preferred embodiments it is desirable to kill at least some of the lice prior to removing the dried agent. For most driable pediculostatic agents, at least some of the lice can be killed by leaving the dried agent on the lice and hair for at least about 8 hours. For some driable pediculostatic agents, shorter periods might be sufficient. The amount of time necessary for a particular agent to kill a louse can be readily determined using the in vitro assays described infra.

Heat has been implicated as one method of killing lice. Accordingly, once the agent has been dried, heat from a hair implement, such as a blow dryer, can be applied to the head to facilitate killing of the lice. Since the lice remain immobile, they cannot escape the heat. However, the use of heat should be exercised with care, so as to avoid scalding or burning the head or other treatment site. Moreover, the driable pediculostatic agent preferably should not contain solvents or other ingredients that are inflammable at the temperatures encountered during heating.

After the dried agent has been left on the hair for a sufficient period of time, typically 8 hours or overnight, it can be removed. Having immobilized all crawling adults, and having killed some proportion thereof, the agent has rendered the adults readily removable by combing. Because only adults migrate from host to host, and because more than a week is required for maturation of any newly-hatching nits, the overnight treatment renders the patient noncontagious for at least one week. Thus, a treatment regimen that includes overnight treatment at least once per week renders the patient completely noncontagious. If the driable pediculostatic agent includes a marker that signals its application (see infra), this could revolutionize treatment of schoolchildren, who are today forbidden in most jurisdictions from attending school with even a single nit: evidence of treatment within the week prior, using the methods of the present invention, would suffice to indicate that the child is noncontagious to classmates.

While the agent can be removed immediately following an overnight treatment, a particular advantage of the method of the invention is that the dried agent is almost undetectable. Thus, it can be left in the hair during the day and conveniently removed at night. This is particularly convenient for treating children, because the agent can be removed in the evening at bath time.

Moreover, leaving the dried agent on the hair during the day further reduces the chance of transmitting the infestation to others.

Rather than having to stay home from school, as presently required by most school districts, infested children could thus attend school with the dried agent in their hair. By incorporating into the driable pediculostatic agent a visible or fluorescent dye, or other easily detectable agent, school officials could readily determine whether the child were "wearing" the treatment, and thus able to attend classes.

In fact, since the agents do not require toxic pediculicides for success, the dried agent can be left on the hair for a few days, or even a week, prior to removal. Thus, in an alternative treatment regimen, the dried pediculostatic agent is left on the hair for a week. The first-applied agent is then removed, and the treatment repeated, or alternatively the initially applied agent is left in the hair as a second application of pediculostatic agent is undertaken. The second treatment immobilizes, kills, and permits removal of any adults that had matured in the week following initial application.

It has now further been discovered that prolonged exposure—that is, greater than 8 hour exposure—to the dried pediculostatic agent inhibits nit hatching. Because newly hatched instars must obtain a blood meal shortly after hatching, prolonged exposure to dried pediculostatic agent, with concomitant inhibition of hatching during that period, can serve to starve embryos within the nit, preventing a new cycle of infestation. A single, prolonged, exposure to dried pediculostatic agent can thus serve to eradicate the infestation. Furthermore, because the nits, so treated, will not give rise to reinfestation of the treated patient, removal of nits is not required in these embodiments, either to effect cure or to prevent contagious transmission.

Thus, in another aspect, the dried pediculostatic agent can be left on the affected area for days, or even a week or more, even up to a month, prior to removal by combing, washing, or combination thereof. Treatment can then be repeated, with the newly-applied and newly-dried pediculostatic agent again left in contact with the hair for days, or even a week or more, prior to removal.

Optionally, the dried pediculostatic agent can be left on the hair for days, or even a week or more, and the treatment continued by further application of pediculostatic agent, optionally followed by combing, and then followed by drying, without the intervening removal of the earlier-applied pediculostatic agent.

In this way, all stages of the louse life cycle can be eradicated, curing the infestation. Of course, agents containing pediculicides should be removed according to the recommended usage instructions for the particular pediculicide. A preferred application schedule for such prolonged exposure to dried pediculostatic agent is once per week; a regimen consisting of two treatments, repeated at one week intervals, is often sufficient to effect full cure.

A further advantage of such prolonged contact with dried pediculostatic agent is that newly-laid nits appear unable to adhere to hair shafts coated with the dried pediculostatic agents of the present invention, deterring reinitiation of infestation through egg laying by adult lice acquired from other patients in the period between applications of driable pediculostatic agent.

Another advantage of using the driable pediculostatic agents according to the methods of the invention is that the head need not be covered during overnight treatment. Since the agent is dried onto the hair and scalp, it does not come off during sleep or soak or stain bed pillows and linens. Thus, the methods of the invention are far easier and convenient than many of the "home" remedies that require overnight application of greasy, non-driable materials such as olive oil, mayonnaise, etc.

The dried agent can be conveniently removed by washing the hair with water, optionally with the aid of soaps, shampoos or conditioners. In this embodiment, the lice simply wash away with the agent. Alternatively, the lice and/or nits can be removed by combing the hair with a fine-toothed delousing comb prior to washing out the dried agent. If combing is used, any remaining dried agent can be removed by washing the hair.

Driable pediculostatic agents useful in the methods and kits of the present invention are characterized by their ability to induce an immersion reflex in lice in their wet form and to keep the lice in the immersion reflex once dried. The following in vitro test can be conveniently used to determine whether any individual agent is a pediculostatic agent, and can further be used for routine screening of agents—such as those from natural products libraries and combinatorial chemical libraries—to identify those that can be used in the methods, compositions, and kits of the present invention:

1. Contact a louse with an agent suspected of being a pediculostatic agent; and
2. Observe whether the louse becomes immobile.

Observations can readily be performed using a standard inexpensive light microscope with 10× or 40× magnification. The length of time necessary to render the louse completely immobile, in minutes, is the Immersion Reflex Index of the agent tested.

Once it has been determined that an agent is a pediculostatic agent, the following in vitro test can be conveniently used to determine whether the agent is a driable pediculostatic agent useful in the methods and kits of the invention:

1. Contact a louse with a pediculostatic agent for a period of time sufficient to immobilize the louse (i.e., for at least 1× the Immersion Reflex Index of the agent);
2. Dry the agent onto the louse, either by air-drying or by application of heat, and observe whether the louse remains immobilized.

If the louse does not regain mobility for an extended period of time when encased in the dried agent, (i.e., about 20 to 60 min.), the agent is a suitable driable pediculostatic agent. The period of time necessary for a particular dried agent to kill the louse can be conveniently determined by rinsing the dried agent off lice as a function of time and observing whether the rinsed lice regain mobility upon drying off.

The driable pediculostatic agents of the present invention typically have an Immersion Reflex Index of no more than 120 minutes. For preferred agents, the Index is 5 minutes or less. For the most preferred agents, the Index can be as low as 0.1 minute, or even lower.

The driable pediculostatic agents of the invention are typically compositions comprising one or more non-volatile compounds that are capable of keeping lice in the immersion reflex (i.e., immobile) once volatile solvents have been removed by drying. While it is convenient to envision that the non-volatile compounds encase the louse in a film or coating, the invention is not intended to be bound by any theory of operation. Any non-volatile agents that do not permit lice to recover from the immersion reflex once dried onto the lice, no matter by what means, are suitable non-volatile agents for use in the driable pediculostatic agents of the invention. Surfactants, lipid materials and alkanols are preferred non-volatile compounds for use in driable pediculostatic agents according to the invention, as will be described more fully below.

The driable pediculostatic agents of the present invention generally comprise pharmaceutically or cosmetically acceptable compositions suitable for topical application to the hair, body and scalp of animals and humans which induce an immersion reflex effect in lice and which cause the lice to remain immobile when the agent dries. In a preferred embodiment, the driable pediculostatic agent is a water-soluble liquid or is incorporated into a liquid or semisolid composition which is flowable or spreadable over the scalp when in its wet form. These compositions are convenient in use, and are an effective medium for coating the lice and scalp.

There are a number of acceptable formulations suitable for use in the present invention, including but not limited to, solutions, lotions, sprays, creams, ointments, emollients, salves, and gels. Descriptions of non-limiting examples of suitable formulations may be found in the PHYSICIAN'S DESK REFERENCE, Medical Economics Co., Pub., Oradell, N.J., PHARMACEUTICAL DOSAGE FORMS AND DRUG DELIVERY SYSTEMS, 1995, Williams & Wilkins, Malvern, Pa. and THE NATIONAL FORMULARY, American Pharmaceutical Association, Pub., Washington, D.C., each of which is incorporated herein by reference in its entirety.

The driable pediculostatic agent is preferably transparent or translucent in order to facilitate observation of the area being treated, and is preferably easily driable and easily removed once dried, such as by rinsing with water, or is readily washed out using a shampoo. In general, the driable pediculostatic agent used in the present invention is a liquid or semisolid that, upon drying, presents a barrier that prevents the transfer of oxygen to the lice.

While the driable pediculostatic agents of the invention are preferably water-soluble or aqueous-based, water by itself is not a suitable driable pediculostatic agent. While water triggers the immersion reflex, upon drying the lice recover and regain mobility.

It has been found that aqueous or organic compositions containing surfactants are effective driable pediculostatic agents. While not intending to be bound by any particular theory of operation, it is believed that the surfactant not only triggers the immersion reflex by increasing the ability of the water to effectively coat the lice, thereby blocking their breathing apparatus, but it also covers the lice with a film or coating of surfactant which blocks their breathing apparatus upon evaporation of the solvents from the composition. Once dried, this film encases the louse, blocking its ability to breathe until the dried agent is removed, such as would typically occur by resolubilization.

Thus, in a preferred embodiment, the driable pediculostatic agent of the present invention is a composition containing one or more surfactants. Typically, the surfactant is present in an amount of about 0.1 wt % to 80 wt %, preferably about 1 wt % to 50 wt % In some instances, the surfactant can be applied neat and caused to form a film on the lice by application of heat.

The amount of surfactant optimal for use in a composition may depend upon such factors as the particular surfactant and the solvent system used. The optimal amount can be readily determined by routine experimentation using the above-described in vitro tests. The literature contains numerous examples of specific surfactant compositions which are suitable for use in the present invention. Examples are found in U.S. Pat. Nos. 5,288,483; 4,495,079; 5,034,218; 5,656, 280; 5,284,833; 5,562,912; and 5,480,633, each of which is incorporated herein in its entirety by reference.

Non-limiting examples of suitable classes of surfactants that can be used in the driable pediculostatic agents include wetting agents, surface tension depressants, detergents, dispersing agents, emulsifiers, and quaternary ammonium antiseptics. Non-limiting examples of suitable surfactants include anionic agents, cationic agents, amphoteric agents, zwitterionic agents, and nonionic agents.

Anionic surfactants suitable for use in the driable pediculostatic agents of the invention include, but are not limited to, those described in McCutcheon's *Detergents and Emulsifiers,* 1979, M.C. Publishing Co., North American Edition; Schwartz et al., 1949, *Surface Active Agents, Their Chemistry and Technology*; and U.S. Pat. Nos. 3,929,678; 5,858,383, and 6,001,339, each of which is incorporated herein in its entirety by reference. A preferred anionic surfactant for use in the present invention is sodium lauryl sulfate, which can conveniently be used in an aqueous solution at a concentration from about 1 to 30% by weight, preferably at about 1 wt % to 20 wt %, or even in the range of 1 wt % to 10 wt % or 1 wt % to 5 wt %.

Non-limiting examples of nonionic surfactants include, but are not limited to, fatty alcohols such as lauryl alcohol, cetyl alcohol and stearyl alcohol, glyceryl esters (such as mono, di and tri glycerides), fatty acid esters of fatty alcohols and other alcohols such as polyalkylene glycols (including propylene glycol and polyethylene glycol) sorbitan, and sucrose. Examples of nonionic surfactants suitable for use in the driable pediculostatic agents of the invention include those described in U.S. Pat. Nos. 5,858, 383 and 6,001,339, the disclosure of each of which is incorporated herein by reference. Propylene glycol can be conveniently used in an aqueous solution at a concentration from 1 to 80% by weight. A preferred propylene glycol concentration is 10 to 50% by weight.

Cationic surfactants suitable for use in the driable pediculostatic agents of the present invention include, but are not limited to, quaternary ammonium salts, fatty amines and mixtures thereof. Suitable exemplary quaternary ammonium salts and fatty amines include, but are not limited to, those described in McCUTCHEON'S *Detergents & Emulsifiers,* 1979, M.C. Publishing Co., North American Edition; Schwartz et al., 1949, *Surface Active Agents, Their Chemistry and Technology*, Interscience Publishers, New York, and U.S. Pat. Nos. 3,155,591; 3,929,678; 3,959,461; 4,387, 090; 5,288,483; 5,858,383, and 6,001,339, the disclosure of each of which is incorporated herein by reference.

Other examples of suitable surfactants are Span 65 (sorbitan tristearate), Span 60 (sorbitan monostearate), Span 40 (sorbitan monopalmitate), sodium bis-(2-ethylhexyl) sulfosuccinate, butylene glycol distearate, and Tween 80 (polysorbate 80).

An antifoaming agent can be optionally included in the surfactant composition, an example of which is silicone fluid, or other silicone polymers, such as those described in U.S. Pat. No. 5,288,484, incorporated herein by reference in its entirety In another embodiment, the driable pediculostatic agent of the invention is a composition comprising a non-volatile lipid material, a non-volatile fatty alcohol, a non-volatile fatty ester or mixtures thereof. Suitable lipid materials, which are typically used in gel-type compositions, include, but are not limited to, fatty materials consisting of acids, acid derivatives, alcohols, esters, ethers, ketones, amides and mixtures thereof, typically having carbon chain lengths of from about 12 to 22, preferably from about 16 to about 18. Additional useful lipid materials are described in *Bailey's Industrial Oil and Fat Products*, S. Swern, ed., 3rd Ed., 1979, which is incorporated herein by reference in its entirety.

Suitable non-volatile fatty alcohols are disclosed in U.S. Pat. Nos. 5,288,483; 4,165,369; and 3,155,591; British Patent 1,532,585; Fukushima et al., 1983, Cosmetics & Toiletries 98:89–102 and Hunting, *Encyclopedia of Conditioning Rinse Ingredients*, at 204 (1987), each of which is incorporated herein by reference in its entirety. Additional examples of suitable non-volatile fatty alcohols include C12–C16 alcohols, ceteryl alcohol, cetyl alcohol, isostearyl alcohol, lanolin alcohol, lauryl alcohol, olelyl alcohol, stearyl alcohol and mixtures thereof. Preferred are cetyl alcohol, stearyl alcohol and mixtures thereof. A particularly preferred fatty alcohol is a mixture of cetyl alcohol and stearyl alcohol containing from about 55 wt % to about 65 wt % cetyl alcohol.

Suitable non-volatile fatty esters are disclosed in U.S. Pat. Nos. 5,288,483 and 3,341,465, which are incorporated herein by reference in their entireties. Additional examples of suitable non-volatile fatty esters include cetyl lactate, cetyl octonoate, cetyl palmitate, cetyl stearate, glyceryl monostearate, glyceryl laurate, glyceryl myristate, glyceryl oleate, glyceryl stearate, glyceryl monoacetate and mixtures thereof. Preferred are cetyl palmitate, glycerol monostearate and mixtures thereof.

Typically, the lipid material, fatty alcohol, fatty ester or mixture thereof comprises from about 0.1 wt % to about 80 wt %, usually about 0.5 wt % to about 10 wt % of the composition, preferably from about 1 wt % to about 5 wt % of the composition. Alternatively, the lipid material, fatty alcohol, fatty ester or a mixture thereof can be applied neat and caused to form a film on the lice by application of heat.

Those of skill in the art will recognize that the optimal amount of lipid, fatty alcohol, fatty ester or mixture used will depend on, among other factors, the specific lipids, fatty alcohols and fatty esters and the composition of the solvent system. The optimal amount can be readily determined by routine experimentation using the above-described in vitro tests.

As will be appreciated by those of skill in the art, since the driable pediculostatic agent must be capable of being dried, the nature of the solvents comprising the agents is an important feature. While in many instances water will be used as the solvent, water is not a preferred solvent because heat must typically be used to expedite the drying of water-based agents.

To hasten the drying time, or to provide an agent that can be conveniently air-dried without applying heat, different solvent systems can be used. For example, the solvent can be a mixture of water and a volatile organic solvent, such as a C2–C6 alkanol, phenyl C2–C6 alkanol, C2–C6 alkandiol, phenyl C2–C6 alkandiol, C1–C6 ether, C1–C6 ketone or other well-known volatile solvent. Alternatively, volatile organic solvents can be used neat to dissolve the surfactant, lipid material, fatty alcohol or fatty ester. The only requirement of the solvent system is that the components of the composition be soluble in it and that it be fairly easily evaporated, with or without the aid of moderate heat (such as that produced by a hair-dryer, electric curlers, etc.). In preferred embodiments the solvents comprising the agents are non-toxic and of a viscosity sufficient to effectively coat the hair and lice. Selection of suitable solvent systems is well within the capabilities of those of skill in the art. When heat will be used to aid drying of the agent, the solvents are preferably not inflammable at the applied drying temperature.

The driable pediculostatic agents of the present invention can be used singly or in combination, and can optionally include other components such as thickeners, penetration enhancers, conditioners, osmotic adjusters, acids, bases, buffering agents, skin protectants, stabilizers, antioxidants, coloring agents, preservatives, and fragrances. Thickeners can be included in the driable pediculostatic agents of the invention for decreasing the tendency of the composition to flow away from the treated area. Non-limiting examples of thickeners include cetyl alcohol, stearyl alcohol, petrolatum, glyceryl monooleate, myristyl alcohol and isopropyl palmitate. Other hydrophillic thickeners include polysaccharide gums, an example of which is xanthan gum. Non-limiting examples of preservatives include methyl paraben, propylparaben, and butylparaben. A non-limiting example of an acid is citric acid. Non-limiting examples of coloring agents include FD&C Green No. 8, FD&C Green No. 3, D&C Violet No. 2, and D&C Red No. 3.

Additional optional ingredients that can be used in the driable pediculostatic agents of the invention can be found, for example, in *Pharmaceutical Dosage Forms and Drug Delivery Systems,* 6th Ed., Ansel et al., eds., Lea & Febinger, 1995, incorporated herein by reference in its entirety Commercially available products such as soaps, skin cleansers, lotions, moisturizers, conditioners and shampoos that are non-toxic and pharmaceutically acceptable for topical application may also be used as driable pediculostatic agents, provided that when dried they keep the lice in the immersion reflex. These are preferably applied in their undiluted state and without agitation in order to minimize the formation of foam. The presence of air in the foam or suds can provide oxygen to the lice and therefore lessen the ability of the agent to stun the lice.

Certain compositions that are designed to foam, however, particularly those that are applied as a collapsing foam, such as hair mousse compositions, can usefully be used as driable pediculostatic agents provided that, when applied, they induce the immersion reflex and that when dried, they keep the lice in the immersion reflex. Hair mousse compositions are described in U.S. Pat. Nos. 5,783,202; 5,066,481; 6,001,339; 4,913,893; 5,681,546, incorporated herein by reference in their entireties; such compositions can readily be tested for their ability to serve as driable pediculostatic agents using the tests set forth supra.

In a preferred embodiment of the invention, the driable pediculostatic agent is an aqueous-based composition comprising one or more surfactants and one or more alkanols. Typically, the surfactant-alkanol composition comprises about 0.1 wt % to 80 wt % surfactant and about 0.1 wt % to 80 wt % alkanol. Preferably, the composition is an aqueous-based composition comprising at least about 50 wt % water.

An example of a suitable alkanol-surfactant driable pediculostatic agent is BABY MAGIC® baby shampoo (Mennen Co., Morristown, N.J.) which contains water, polysorbate 20, sodium lauryl sulfate, lauroamphoglycinate, polysorbate 80, PEG-150 distearate, fragrance, citric acid, and quaternium 15. In use, the shampoo is applied in the absence of water in order to avoid foaming and dried onto the hair with a blow dryer.

Another example of an alkanol-surfactant driable pediculostatic agent suitable for use in the present invention is SUAVE® Baby Care bath soap tear-free formula (Helene Curtis, Inc., Chicago, Ill.) which contains water, PEG-80, sorbitan laurate, sodium tridecyl sulfate, cocamidopropyl hydroxysultaine, disodium lauroamphodiacetate, PEG-150 distearate, sodium lauryl-13 carboxylate, aloe vera gel, quaternium-15, DMDM hydantoin, methylchloro isothiazolinone, methylisothiazolinone, fragrance, citric acid, D&C Violet No. 2, D&C Red No. 3.

The presently most preferred composition for use as a driable pediculostatic agent in the invention is a mixture of water, cetyl alcohol, propylene glycol, sodium lauryl sulfate, stearyl alcohol, methyl paraben, propylparaben, and butylparaben sold commercially as a nonirritating, non-greasy skin cleanser under the trademark CETAPHIL® Cleanser (Galderma Laboratories, Inc., Fort Worth, Tex.).

CETAPHIL® Cleanser is additionally advantageous since it aids in the removal of the nits when in its wet form. While the mechanism for this property is not fully understood, a component or components in CETAPHIL® Cleanser may dissolve or loosen the cement which holds the nits to the hair shaft, and may also make the shaft slippery, thus facilitating the removal of the nits during combing.

CETAPHIL® Cleanser has the ability rapidly to trigger the "immersion reflex" in head lice. Both in vivo and in vitro, lice coated in CETAPHIL® Cleanser became immobilized within 6 seconds. On the patients' scalp, the lice became totally immobilized, floating on the scalp in the Cleanser. They were easily removed by forceps without any effort to escape or to grasp the hair shaft to stay in place. Under the microscope, they were immobile, did not respond to being touched, and lost their normally visible gut motility. They remained immobilized as long as they were in the Cleanser. This phenomenon was observed for periods ranging from 6 seconds to 4 hours. At any point prior to drying the cleanser, the louse could be removed from the Cleanser and usually awakened and resumed crawling. When immersed overnight in CETAPHIL® Cleanser (12 hours) the lice died.

When CETAPHIL® Cleanser was dried onto lice (6 lice tested), the lice remained immobile. When the dried agent was removed by redissolving it in water after 4 hours of contact, the lice recovered and regained mobility. When left on the lice for more than 8 hours before redissolving, the lice died.

While the methods of the invention are effective at treating, removing and preventing crawling lice, they are also effective on nits.

A film of CETAPHIL® Cleanser dried onto nits (n=2) and left on for 8 hours prior to redissolving, killed the nits: i.e., the nits did not hatch. The result was replicated in an in vivo test, further described infra in Example 4. Briefly, dried pediculostatic agent was left on a patient's hair (n=1) for one week. Upon combing with a fine-toothed louse comb at one week, there was significant increase in the percentage of embryo-containing nits among the removed nits. While not intending to bound by any theory of operation, it is believed that the nit is prevented from opening during the entire period of contact with the dried pediculostatic agent, but that the agent does not significantly interfere with growth and maturation of the embryo. Because the embryo must obtain a blood meal shortly after hatching, failure to emerge causes death of the embryo and progressive accumulation of embryo-containing nits. Alternatively or in addition, it is possible that the dried pediculostatic agent starves the embryo for oxygen, which must pass into the nit from the external milieu. Whatever the mechanism of action, however, it has now been discovered that prolonging exposure to the dried pediculostatic agent prevents hatching of nits and death of the embryos therein.

As a result, in those embodiments of the present invention in which contact with dried pediculostatic agent is sufficiently prolonged as to kill nits, nit removal by combing is not required as part of the treatment regimen.

The invention can also incorporate a system for verifying whether the dried pediculostatic agent has been applied. This is an important feature for certain populations where cross-contamination is known to occur, such as in a grade school setting. It is particularly important in embodiments of the invention in which nit removal is neither required for treatment nor practiced, and thus where reliance upon nit absence—presently the critical indicium of noncontagious status—is no longer diagnostic of effective treatment.

The driable pediculostatic agent is optionally combined with a dye that will temporarily remain on and mark the hair and/or scalp and/or nits after drying, in order to verify that the agent has been applied. The dye is present at a concentration that will leave an observable mark (e.g. 0.1 to 1 wt % in the driable pediculostatic formulation) and preferably is non-volatile and non-toxic. The dye can be fluorescent, and thus visible only under an ultraviolet light, so that the presence can be detected but will not alter the color of the patient's hair. Non-limiting examples of suitable dyes include those described in U.S. Pat. Nos. 4,610,806 and 5,302,371. Additional suitable dyes can be found in the Molecular Probes (Eugene Oreg.) catalogue and the references cited therein.

Alternatively, the dye can be visible in natural light, with the color chosen to be attractive, either by mimicking a natural hair color different from the patient's, or alternatively by its unnatural color, the latter particularly suitable as a novelty that will be attractive to children. Alternatively or in addition to dyes, the composition can include glitter, or other particles that are visibly detectably. A nonlimiting example is described in U.S. Pat. No. 5,853,706, the disclosure of which is incorporated herein by reference.

Optionally, a driable pediculostatic agent and a conventional pediculicide can be coadministered. In one embodiment of the method of the invention, a conventional pediculicidal active ingredient can be incorporated into the driable pediculostatic formulation described herein. The active ingredients can be used at levels of from about 0.25% to about 2.5%. Exemplary useful pediculicidal agents include natural pyrethrins, pyrethroids, permethrin, lindane, malathion, carbaryl, ivermectin and combinations thereof. Piperonyl butoxide can be optionally included at levels of from about 1 wt % to 5 wt % to hinder the development of resistance of the pediculicidal additives.

In an alternative embodiment, a pediculicidal agent can be applied first, followed by application of a driable pediculostatic composition, or vice versa. Such compositions are well known in the art and include, but are not limited to, RID® (Pfizer Inc., New York, N.Y.), NIX® (Warner-Lambert, Harristown, N.J.), KWELL® (Reed and Carnick, Jersey City, N.J.), A-200® (Hogil, Purchase, N.Y.), PRONTO® (Del Pharmaceuticals, Uniondale, N.Y.), LINDAINE® (Alpharma, Baltimore, Md.), CLEAR® (Care Technologies, Inc., Greenwich, Conn.), and those described in U.S. Pat. No. 5,292,504, which is incorporated herein by reference in its entirety. If the pediculicidal agent is applied first, it can be rinsed from the hair prior to application of the driable pediculostatic agent, or can be dried onto the hair along with the driable pediculostatic agent.

In another aspect, the invention provides kits for the treatment, removal or prevention of lice. One kit according to the invention includes an amount of a driable pediculostatic agent according to the invention, packaged in association with instructions for use in the methods described herein. The instructions can conveniently be affixed to a bottle or container containing the driable pediculostatic agent, and the kit can, if the instructions are so affixed directly to the container, exclude further packaging. The instructions can conveniently be abbreviated by provision of an Internet web site address (URL), at which site the user can obtain more detailed instructions, and/or provision of a telephone number, preferably a toll-free telephone number, email address, or even a radio frequency at which the user can obtain more detailed instructions, either directly, or via an automatic response system.

The kit can optionally including a comb for removing excess agent or a delousing comb.

Another kit according to the invention includes an amount of a driable pediculostatic agent suitable for at least one treatment (about 8 ounces) and a comb for removing excess agent, and optionally at least one delousing comb suitable for removing adult lice and nits. Alternatively, the kits can contain ingredients in quantities suitable that when they are mixed together, either with or without the addition of water or other solvents, provide an amount of driable pediculostatic agent sufficient for at least one application or treatment. Examples of suitable delousing combs are known in the art and include ACU-MED® Lice Comb (Health Enterprises, North Attleboro, Mass.), LICEMEISTER® Lice Comb (National Pediculosis Association), MEDI-SWEEP® Lice Comb (U.S. Pat. No. 4,612,944), and dog and/or cat FLEA COMB® (Classic Products, Oxnard, Calif.), each of which is incorporated herein by reference in its entirety. The comb is preferably constructed of rigid material such as metal or plastic. In a preferred embodiment, the comb is inexpensive and designed to be disposable after a single use, in order to prevent contamination. In another embodiment the comb has a removable, and preferably disposable, piece having a plurality of teeth which attaches to a handle portion such as described in U.S. Pat. No. 5,636,646, incorporated herein by reference in its entirety.

Of course, other components such as pediculicidal agents, markers such as fluorescent dyes, shower caps, paper towels, etc. can also be included in the kits of the invention. Typically, the kit will contain a quantity of driable pediculostatic agent to completely eradicate a lice infestation, thereby providing an effective treatment for lice.

While the invention has been described in terms of removal, treatment or prophylaxis of head lice, it will be appreciated that the methods and kits of the invention can be used as described for the treatment, removal or prevention of other types of lice infestations, including body and pubic lice. Moreover, the methods and kits can be used to treat, remove or prevent infestations of other insects, mites, ectoparasites or other bugs or pests which evince an immersion reflex when immersed in water, and/or which suffocate when coated with a dried driable pediculostatic agent, such, as for example, ticks, fleas, etc.

Other features of the invention will become apparent in the course of the following descriptions of exemplary embodiments which are given for illustration of the invention and are not intended to be limiting thereof.

EXAMPLE 1

CETAPHIL® Cleanser Triggers the Immersion Reflex in Lice within Seconds

Ten crawling lice were obtained from patients with head lice and each one placed on a separate microscope slide for observation under a microscope at 10× or 40× power. Each louse was placed in a drop of CETAPHIL® Cleanser for up to 4 hours. All of them exhibited the same response. Within 6 seconds of application, they stopped all spontaneous movement. Usually within 30 seconds, and always within 60 seconds, they would not respond to contact by a probe and ceased previously visible gastrointestinal motility. They remained in this state of suspended animation as long as they were kept in wet CETAPHIL® Cleanser. If the louse was pulled to the side of the drop, it could be seen that the CETAPHIL® Cleanser formed an adherent layer surrounding and conforming to the body and limbs. When the lice were removed from the CETAPHIL® Cleanser and allowed to dry off, they usually awoke and all prior activity. Thus, the lice were stunned but were not killed by the Cleanser. The longer the louse was coated, the longer it took to awaken after removed from the Cleanser. After five of the lice were placed in the Cleanser overnight, they were all dead following 12 hours of immersion in the Cleanser. To reliably kill head lice with the Cleanser, immersion for periods longer than 4 hours were required.

EXAMPLE 2

Dried CETAPHIL® Cleanser Maintains the Immersion Reflex in Lice

Six crawling lice were obtained from patients with head lice and each placed in a drop of CETAPHIL® Cleanser as described in EXAMPLE 1. After 2 min., the cleanser was dried onto the lice by air drying (4 lice) or gentle warm air from a hair dryer (2 lice). The lice continued to demonstrate the immersion reflex, i.e., they remained immobile the entire time they were encased in the dried cleanser, as judged by examination under a microscope.

When the dried agent was removed at fewer than four hours by re-solubilizing with water and gentle mechanical stirring, the lice recovered and gained mobility. Lice encased in the dried agent for at least 8 hours prior to removal by re-solubilizing died.

Two nits encased in dried CETAPHIL® Cleanser prior to removal by re-solubilizing failed to hatch.

EXAMPLE 3

Clinical Use of a Driable Pediculostatic Agent in the Treatment of Head Lice

A group of 23 patients with active head lice infestations were treated with CETAPHIL® Cleanser by soaking the hair and scalp with the cleanser and removing any excess by combing with a delousing comb. The cleanser was then dried onto the hair with a blow dryer and the dried cleanser allowed to remain on the hair for 8 to 24 hours prior to removal by shampooing. All patients gave a history of symptoms of lice and/or recent exposure to a close family member or friend with lice. Some of the patients had previously tried one or several commercially available lice treatments; one patient had tried a buzz haircut. All patients or their parents signed informed consent forms prior to entry into the study. The patients ranged in age from 3 years to 37 years, with most of the patients being around 4 to 7 years old.

All treatments were done at the patients' homes, usually by the parent. Treatment was done once weekly until no lice were present. All of the patient's family members were treated with at least one treatment to see if they had lice or nits in their data collection. If identified as affected, then they were added to the study.

Method of Application

All patients in the study were asked to follow the following protocol once weekly until requested to stop by the research director:

1) Start with dry hair;
2) Use a wide-toothed comb to detangle the hair;
3) Apply CETAPHIL® Cleanser thoroughly throughout the scalp to totally soak the scalp and hair (usually this requires 6 oz. for short hair and 12 oz. for long hair);
4) Wait 2 minutes;
5) Use a wide-toothed comb to detangle hair and then comb hair with a fine-toothed delousing comb to remove excess CETAPHIL® Cleanser, lice and nits;
6) Place the removed cleanser on paper towels, seal the towels in a plastic zipper bag and return the bags to the research director for analysis;
7) Dry the Cleanser onto the hair with a blow-dryer;
8) After at least 8 hours (conveniently overnight), remove the dried cleanser by rinsing with water, shampoo and/or conditioner, as desired.

During the course of treatment, all patients were advised to wear clean clothes after each treatment, to launder all dirty clothes and to put clean sheets on the bed. Patients were also requested to sanitize all combs and brushes daily by soaking for minutes in rubbing alcohol and to sanitize all hair ribbons, scrunchies, etc. and hats by placing in plastic bags for 14 days. Patients were further advised not to share combs, brushes, hats or other hair items with anyone and to avoid friends or classmates showing symptoms of lice infestation.

Data Analysis

Each bag received from patients was opened and all lice and nits present counted and recorded on a computerized data form. The total number of nits present, the number of instars present and the number of adult lice present were recorded.

Determination of Cure

Complete lice removal was defined as meeting three criteria:

1) No lice in the data collection from the paper towels returned after treatment;
2) No further symptoms of lice infestation; and
3) No recurrence of lice reported by the patients within 2 months of achieving a zero lice data collection result.

The number of applications to achieve complete lice removal, or cure, is defined as the number of applications that produced lice before the zero lice collection result was achieved. For example, if on the third application there were no lice in the towel data, then it took 2 applications to remove all the lice.

Results

All 23 patients achieved complete lice removal. Of the 23 patients, 20 achieved complete removal after 1 treatment and 3 achieved complete removal after 2 treatments. On average, it took 1 treatment to achieve complete removal. Some of the patients had previously tried pediculicidal treatments without success. A sufficient number of nits were removed to allow the patients to return to school, whereas with the conventional pediculicidal treatments they could not. In some instances, parents had to manually remove a small number of residual nits in order for the patient to return to school. The raw data are shown in TABLE 1, infra:

TABLE 1

| Age | Prior Treatment | No. Treatments Until Cured | Total No. Lice Removed | Total No. Nits Removed |
| --- | --- | --- | --- | --- |
| 7 yrs | Nix ®; Rid ® | 1 | 23 | 188 |
| 8 yrs | Nix ®; Rid ® | 1 | 10 | 10 |
| 12 yrs | Nix ®; Nix ®; Generic; Generic | 1 | 6 | 942 |
| 9 yrs | Nix ®; Generic; Generic; Generic | 1 | 2 | 112 |
| 10 yrs | Nix ®; Generic; Generic; Generic | 1 | 17 | 103 |
| 4 yrs | None | 1 | 2 | 7 |
| 3 yrs | Nix ®; Nix ®; Elmite | 1 | 4 | 0 |
| 4 yrs | Oil: olive, tea; Nix ®; Clear ® | 1 | 7 | 15 |
| 6 yrs | Nix ®; Rid ®; Generic; Generic | 1 | 30 | 333 |
| 32 yrs | Nix ®; Rid ®; Generic; | 1 | 2 | 4 |
| 8 yrs | Nix ®; Rid ®; Generic; Generic | 1 | 10 | 17 |
| 11 yrs | Nix ®; Rid ®; Generic; Generic | 1 | 1 | 43 |
| 7 yrs | None | 1 | 2 | 3 |
| 12 yrs | Rid ® | 1 | 1 | 4 |
| 7 yrs | Nix ®; Rid ®; Vaseline | 1 | 1 | 38 |
| 33 yrs | Nix ®; Rid ®; Vaseline | 1 | 1 | 0 |
| 37 | Nix ®; Rid ®; Vaseline | 1 | 1 | 0 |
| 34 yrs | Nix ® | 1 | 6 | 15 |
| 7 yrs | None | 1 | 1 | 0 |
| 34 yrs | None | 1 | 2 | 2 |
| 8 yrs | Nix ® | 2 | 30 | 75 |
| 6 yrs | Nix ®; Haircut/Buzz | 2 | 2 | 0 |
| 5 yrs | Rid ® | 2 | 2 | 12 |

A total of 163 lice and 1923 nits were removed, yielding an average of 7.1 lice and 83.6 nits per patient. All patients and parents described the process as not unpleasant. All reported immediate relief of itching after the first application. None of the patients complained that the dried agent was unpleasant to wear.

EXAMPLE 4

Extended Exposure to Dried Pediculostatic Agent Inhibits Nit Hatching

A six year old patient with an active lice infestation that had previously been treated unsuccessfully with two different pediculocidal compositions (Nix® and Pronto®) was treated with driable pediculostatic agent as follows.

CETAPHIL® Cleanser was applied to the patient's dry hair in a quantity sufficient fully to wet the hair. After a short interval, the patient's hair was combed with a louse comb. The removed material, which included excess Cleanser, was inspected, revealing 19 first stage instars and 95 nits. The patient's hair was then dried using a blow dryer.

The patient was instructed to leave the hair totally dry for 1 week and then to return to the Research Center for further treatment. On the second day after treatment, however, the patient's hair reportedly became partly wet during bathing. The hair was allowed to air dry, and no additional driable pediculostatic agent was added at that time.

At one week, the patient returned to the Research Center, and the treatment described above was repeated: without any washing or removal of the earlier-applied driable pediculostatic agent, CETAPHIL® Cleanser was applied to the patient's hair in a quantity sufficient fully to wet the hair. After a short interval, the patient's hair was combed with a louse comb, and then dried with a blow dryer.

Upon inspection of the material removed by combing (i.e., removed prior to drying) in this second treatment, a total of 4 second stage instars and 30 nits were counted. Further microscopic inspection of the 30 removed nits revealed the following results:

| Nit Status | Number of Nits | % of Total Nits |
|---|---|---|
| empty, with no nit cover in place | 8 | 27% |
| embryo inside, with nit cover present | 22 | 73% |

The ratio of embryo-containing to embryo-free nits observed with long-term (7 day) incubation in the presence of dried pediculostatic agent, almost 3:1, is substantially different from that typically seen with shorter (e.g., 8–12 hour) incubation, typically about 1:4. This would suggest that hatching of nits—but not the growth and maturation of the embryos therein—is inhibited during contact with the dried pediculostatic agent: as the period of contact is extended, there is thus a progressive accumulation of nits with unhatched embryos. Consistent with this interpretation, the four instars that were observed were all second-stage instars, a stage achieved 5–6 days after hatching, consistent with their hatching during the brief period that the dried pediculostatic agent had been solubilized by the patient's inadvertent hair wetting one day into treatment.

The further microscopic observation that two of the embryo-containing nits had covers that were slightly raised, with the dead embryo extending a limb from thereunder, further suggests that a mechanism for such hatching inhibition might include mechanical inhibition of cover removal.

EXAMPLE 5

Prophylactic Use of Pediculostatic Agents

CETAPHIL® Cleanser is applied as in the previous examples, but on a periodic, preferably weekly, basis in order to prevent re-infestation or to prevent infestation of persons who are uninfected but at risk for catching head lice.

EXAMPLE 6

Treatment at School

Current school policy is immediately to send children home who are discovered to have lice infestation. As an alternative, CETAPHIL® Cleanser is applied to and dried onto the scalp at school and left in place until the child returns home at the end of the day. The agent can then be removed by the child's parents, and the treatment regimen outlined above commenced until the infestation is cured.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

I claim:

1. A method of rendering ectoparasites removable from a subject, said ectoparasites having an immersion reflex, comprising:
    a) applying to an area of the subject's body having the ectoparasites an effective amount of a composition, said composition comprising:
        (i) a driable pediculostatic agent, said driable pediculostatic agent consisting essentially of at least one compound selected from the group consisting of non-volatile surfactants, polar organic compounds, non-volatile fatty alcohols, and non-volatile fatty esters, for a time sufficient to trigger the immersion reflex in said ectoparasites; and
        (ii) a detectable marker, and then
    b) drying said composition with air or with heat.
2. The method of claim 1, wherein said marker is a dye.
3. The method of claim 2, wherein said dye is fluorescent.
4. The method of claim 2, wherein said dye is visible in natural light.
5. The method of claim 4, wherein said dye has a color not naturally found in hair.
6. The method of claim 1, wherein said marker is a visibly detectable particle.
7. The method of claim 6, wherein said visibly detectable particle glitters.
8. The method of claim 1, wherein said ectoparasites are head lice.
9. The method of claim 1, wherein said ectoparasite are pubic lice.
10. The method of claim 1, wherein said ectoparasite are ticks.
11. The method of claim 1, wherein said ectoparasite are mites.
12. The method of claim 1, wherein said dried composition remains on the body for at least 8 hours.
13. The method of claim 1, wherein said driable pediculostatic agent consists essentially of a nonvolatile surfactant.
14. The method of claim 13, wherein said nonvolatile surfactant is a surface tension depressant.
15. The method of claim 13, wherein said nonvolatile surfactant is a wetting agent.
16. A method for prevention of active lice infestations, comprising:
    a) applying to an area of the subject's body at risk of lice infestation an effective amount of a composition, said composition comprising:
        (i) a driable pediculostatic agent, said driable pediculostatic agent consisting essentially of at least one compound selected from the group consisting of non-volatile surfactants, polar organic compounds, non-volatile fatty alcohols, and non-volatile fatty esters, for a time sufficient to trigger the immersion reflex in said ectoparasites; and
        (ii) a detectable marker, and then
    b) drying said composition with air or with heat.
17. The method of claim 16, wherein said marker is a dye.
18. The method of claim 17, wherein said dye is fluorescent.
19. The method of claim 16, wherein said dye is visible in natural light.
20. The method of claim 19, wherein said dye has a color not naturally found in hair.
21. The method of claim 16, wherein said marker is a visibly detectable particle.
22. The method of claim 21, wherein said visibly detectable particle glitters.
23. The method of claim 16, wherein said ectoparasites are head lice.
24. The method of claim 16, wherein said ectoparasite are pubic lice.
25. The method of claim 16, wherein said ectoparasite are ticks.
26. The method of claim 16, wherein said ectoparasite are mites.

27. The method of claim 16, wherein said dried composition remains on the body for at least 8 hours.

28. The method of claim 16, wherein said driable pediculostatic agent consists essentially of a nonvolatile surfactant.

29. The method of claim 16, wherein said nonvolatile surfactant is a surface tension depressant.

30. The method of claim 16, wherein said nonvolatile surfactant is a wetting agent.

31. A kit for the removal, treatment or prevention of lice or nits, comprising:
   a) an amount of a composition comprising a driable pediculostatic agent effective for at least one application, wherein said driable pediculostatic agent consists essentially of at least one compound selected from the group consisting of non-volatile surfactants, polar organic compounds, non-volatile fatty alcohols, and non-volatile fatty esters; and
   b) instructions effective to perform the method of either of claims 1 or 16, wherein said instructions are directly affixed to the container enclosing said composition.

32. The kit of claim 31, wherein said composition further comprises a detectable marker.

33. The method of claim 32, wherein said marker is a dye.

34. The method of claim 33, wherein said dye is fluorescent.

35. The method of claim 33, wherein said dye is visible in natural light.

36. The method of claim 35, wherein said dye has a color not naturally found in hair.

37. The method of claim 32, wherein said marker is a visibly detectable particle.

38. The method of claim 37, wherein said visibly detectable particle glitters.

39. The kit of claim 31, further comprising:
   a lice comb.

* * * * *